United States Patent
Elliott et al.

(10) Patent No.: US 6,607,699 B1
(45) Date of Patent: Aug. 19, 2003

(54) HAIR ROOT COLLECTION KIT

(75) Inventors: James Elliott, Gloucester (CA); Ronald Fourney, Orleans (CA); Susan Borys, Ottawa (CA)

(73) Assignee: Her Majesty the Queen in right of Canada, as represented by the Solicitor General acting through the Commissioner of the Royal Canadian Mounted Police, Ottawa (CA)

( * ) Notice: Subject to any disclaimer, the term of this patent is extended or adjusted under 35 U.S.C. 154(b) by 302 days.

(21) Appl. No.: 09/632,165

(22) Filed: Aug. 3, 2000

(51) Int. Cl.[7] .................. G01N 21/00; B65D 81/02
(52) U.S. Cl. .................. 422/61; 206/206; 206/223; 206/305; 206/460
(58) Field of Search .................. 422/61; 206/206, 206/223, 305, 460, 569, 778

(56) References Cited

U.S. PATENT DOCUMENTS

| | | | | |
|---|---|---|---|---|
| 5,211,286 A | * | 5/1993 | Turner | 206/223 |
| 5,582,298 A | * | 12/1996 | Clayton et al. | 206/460 |
| 5,856,102 A | * | 1/1999 | Bierke-Nelson et al. | 206/223 |
| 6,355,439 B1 | * | 3/2002 | Chung et al. | 428/343 |

FOREIGN PATENT DOCUMENTS

WO        01/18239    *   3/2001

* cited by examiner

Primary Examiner—Jill Warden
Assistant Examiner—LaToya I. Cross
(74) Attorney, Agent, or Firm—George A. Seaby

(57) ABSTRACT

A hair root collection kit for delivering hair samples to a laboratory for DNA analysis of the root sheaths includes a card with an adhesive strip extending thereacross for holding the hair samples on the card. With the hair samples on the card, the root sheaths overlie a non-adhesive impermeable plastic area. The card is covered by a clear plastic cover for protecting the hair during delivery to the laboratory.

7 Claims, 5 Drawing Sheets

HAIR ROOT COLLECTION KIT

BACKGROUND OF THE INVENTION

1. Field of the Invention

This invention relates to a hair root collection kit, and in particular to a hair root collection kit for use in the isolation of DNA from hair roots.

2. Discussion of the Prior Art

The National DNA Data Bank, located in Ottawa, Ontario, Canada and other laboratories worldwide collect and analyze human hair. Analysis involves the microscopic comparison of different hair samples or DNA isolation from hair roots for subsequent analysis. DNA processing from hair typically requires the use of cells contained at the "bulb" or root sheath of pulled hair. Another current procedure using mitochondrial DNA actually uses the hair shaft, but this procedure is more specialized and less discriminating than the DNA method using the root sheath.

A problem with hair is proper preparation of the pulled hair and storage. Typically, numerous hairs (ten or more) are pulled and the root sheaths are cut off and processed for DNA analysis. At present, hair samples are delivered to the laboratory in small sample tins or paper envelopes. Plastic containers and bags are avoided due to static and the possibility of losing hairs when they are pulled from the container.

In the past, hair arriving in a forensic laboratory could be processed on a case by case basis. However, in large forensic laboratories it is not unusual for 100–200 packages of hair to arrive virtually simultaneously. Substantial time delays are experienced for the analyst to locate and carefully remove each hair for processing in 1.5 ml tubes. The hairs are commonly entwined, making it difficult to identify which end of the individual hairs has a root. Moreover, it is difficult to handle single hair samples.

GENERAL DESCRIPTION OF THE INVENTION

An object of the present invention is to provide a solution to the problem of collecting and immobilizing hair samples outlined above in the form of a relatively simple hair root collection kit.

Another object of the invention is to provide a hair sample collection kit which allows for individual hairs to be quickly and easily immobilized in a particular orientation, and which allows for protection from contamination.

Accordingly, the present invention relates to a hair root collection kit comprising a planar base; an adhesive area on said base; and a non-adhesive, impermeable area on said base adapted to receive individual hairs, whereby the hairs can be mounted on the adhesive area with root sheaths thereof overlying the non-adhesive area.

Preferably, the planar base is a paper card, and the strip of adhesive is a length of double faced tape, i.e. a strip of tape with adhesive on both sides thereof. One side of the tape is adhered to the card, and the other side receives the individual strands of hair.

BRIEF DESCRIPTION OF THE DRAWINGS

The invention is described below in greater detail with reference to the accompanying drawings, which illustrate a preferred embodiment of the invention, and wherein.

DESCRIPTION OF THE PREFERRED EMBODIMENT

It will be noted that the hair root collection kit of the present invention is actually used to collect entire hair samples. However, it is only the roots which are required for DNA analysis.

Figure 1:
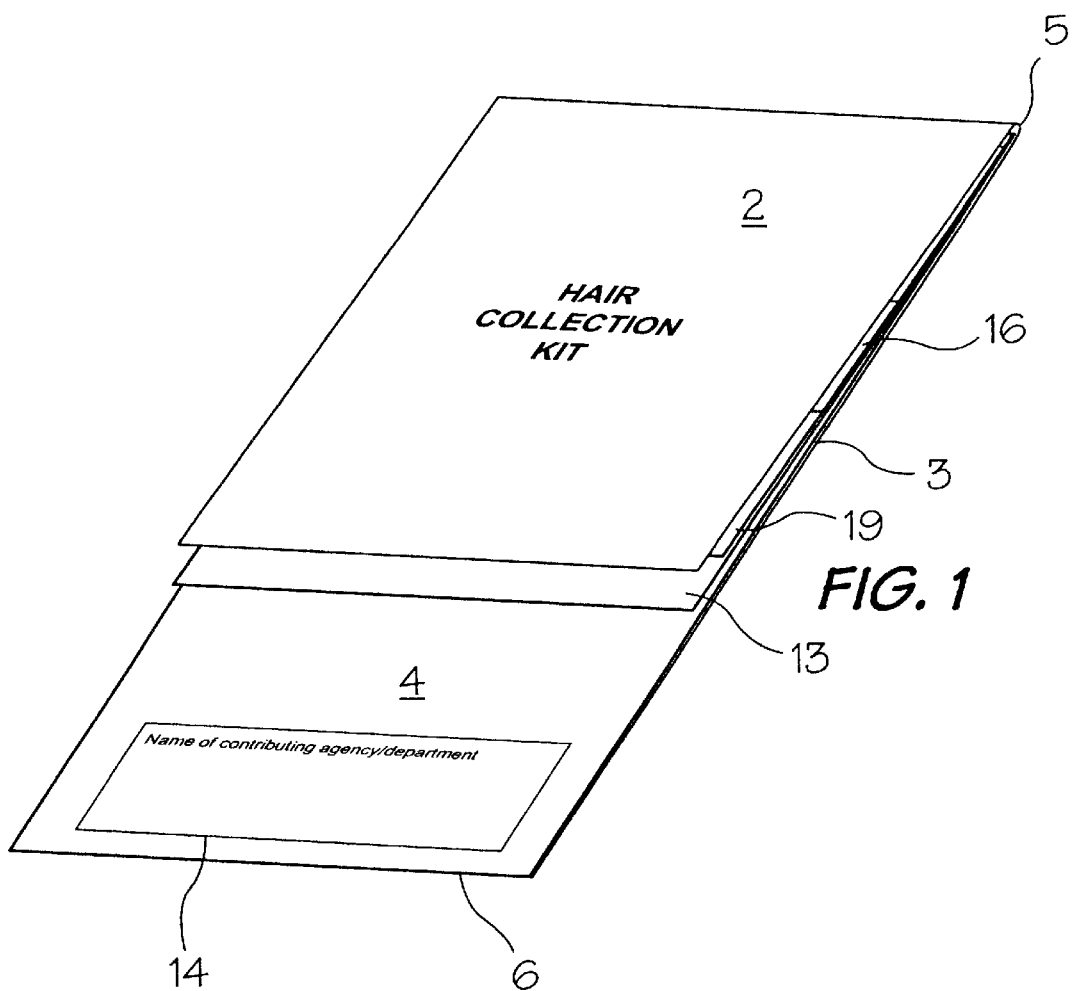
FIG. 1 is an isometric view of a hair root collection kit in accordance with the present invention in the closed condition.
Figure 2:
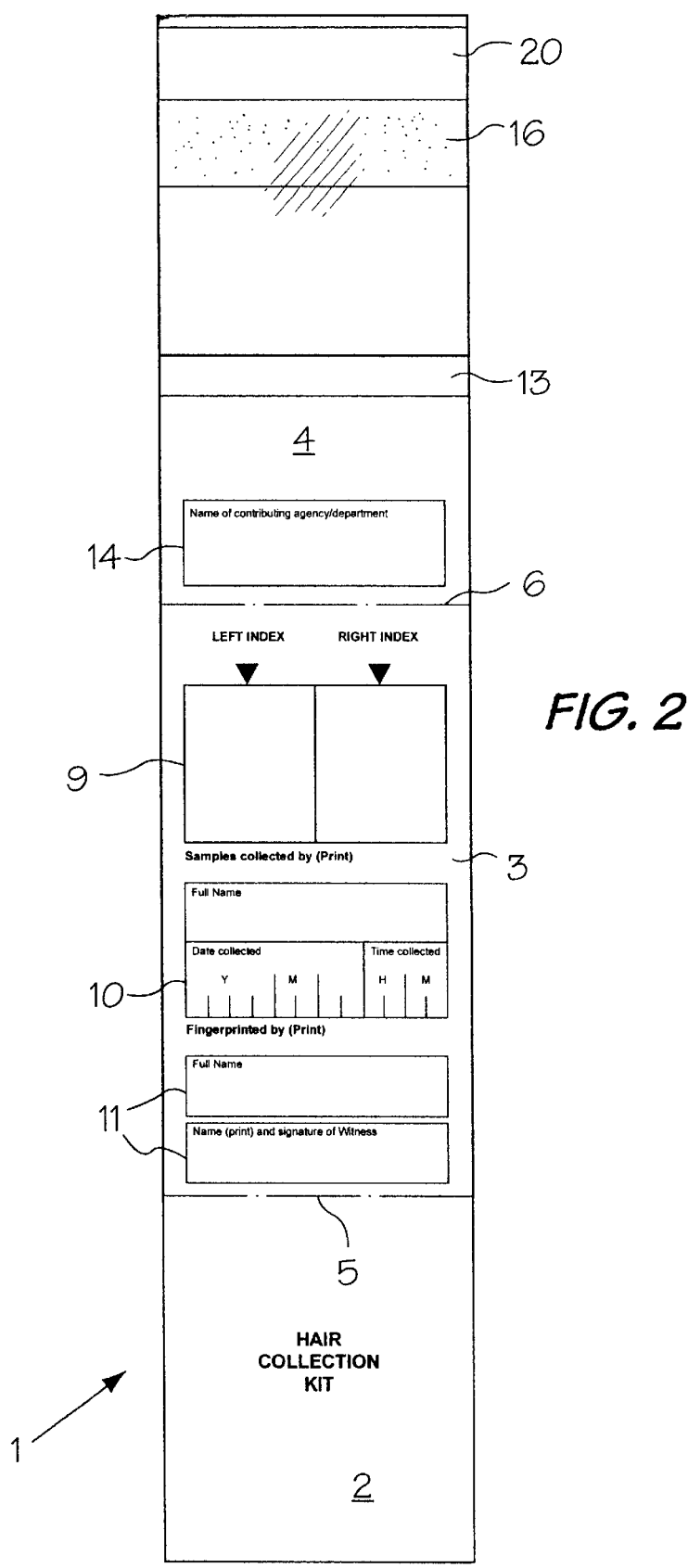
FIG. 2 is a front view of the collection kit of FIG. 1 in a fully open condition.

Referring to FIGS. 1 and 2, the hair root collection kit is formed from a rectangular paper blank generally indicated at 1. The blank 1 is defined by three contiguous panels 2, 3 and 4 which are separated by fold lines 5 and 6. One panel 2 forms an outer or top cover for the kit, when the panels are folded together (FIG. 1) to form a compact article. Indicia 8 on the top cover identify the product.

The central panel 3, which is the lower or back panel when the blank is folded, contains boxes 9, 10 and 11 for use in identifying the party whose hair is carried by the kit, and the person(s) collecting the hair samples and fingerprinting the person whose hair is being collected.

Figure 3:
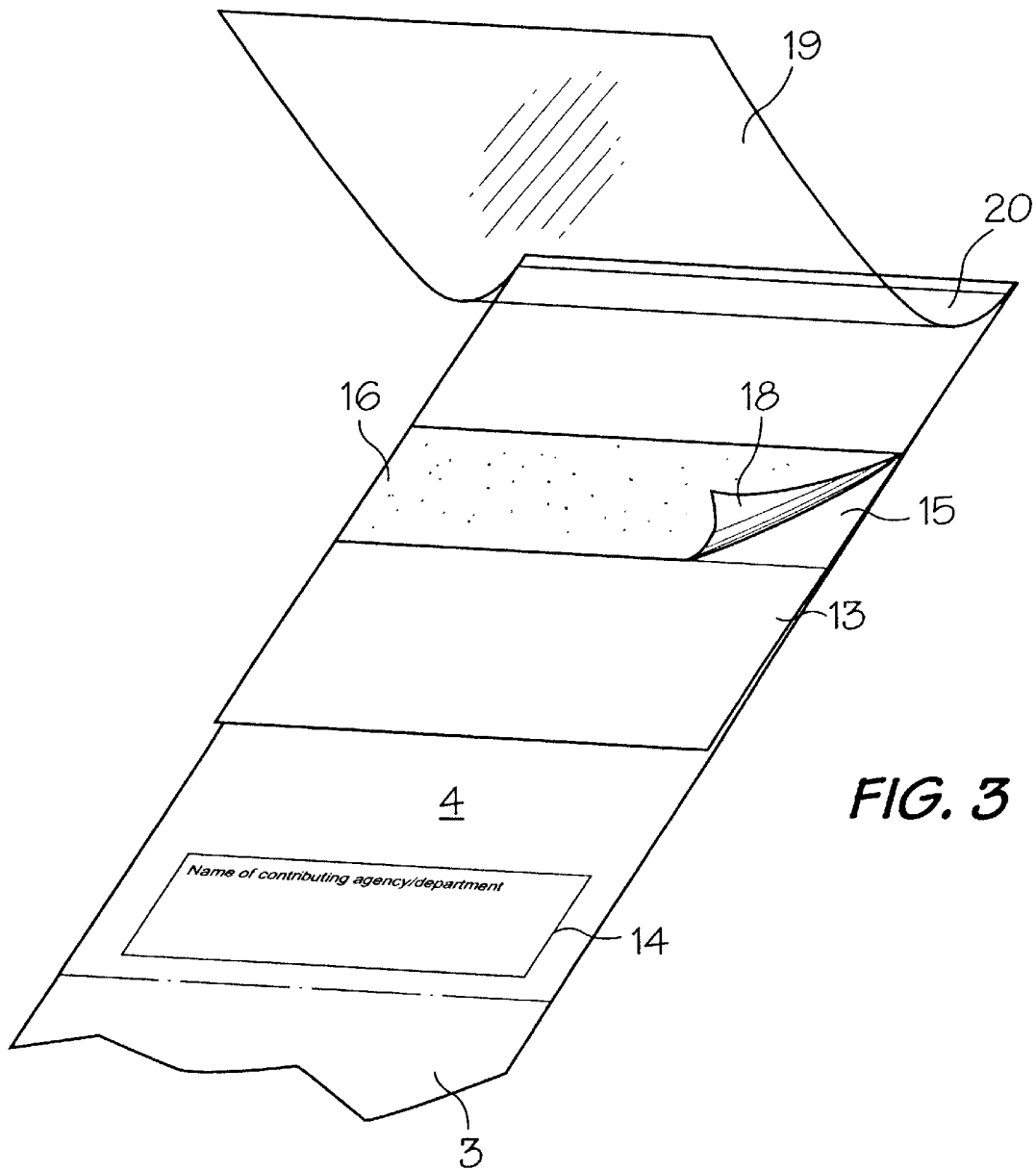
FIG. 3 is an isometric view of a card and cover used in the collection kit of FIGS. 1 and 2 in a party open condition.
Figure 4:
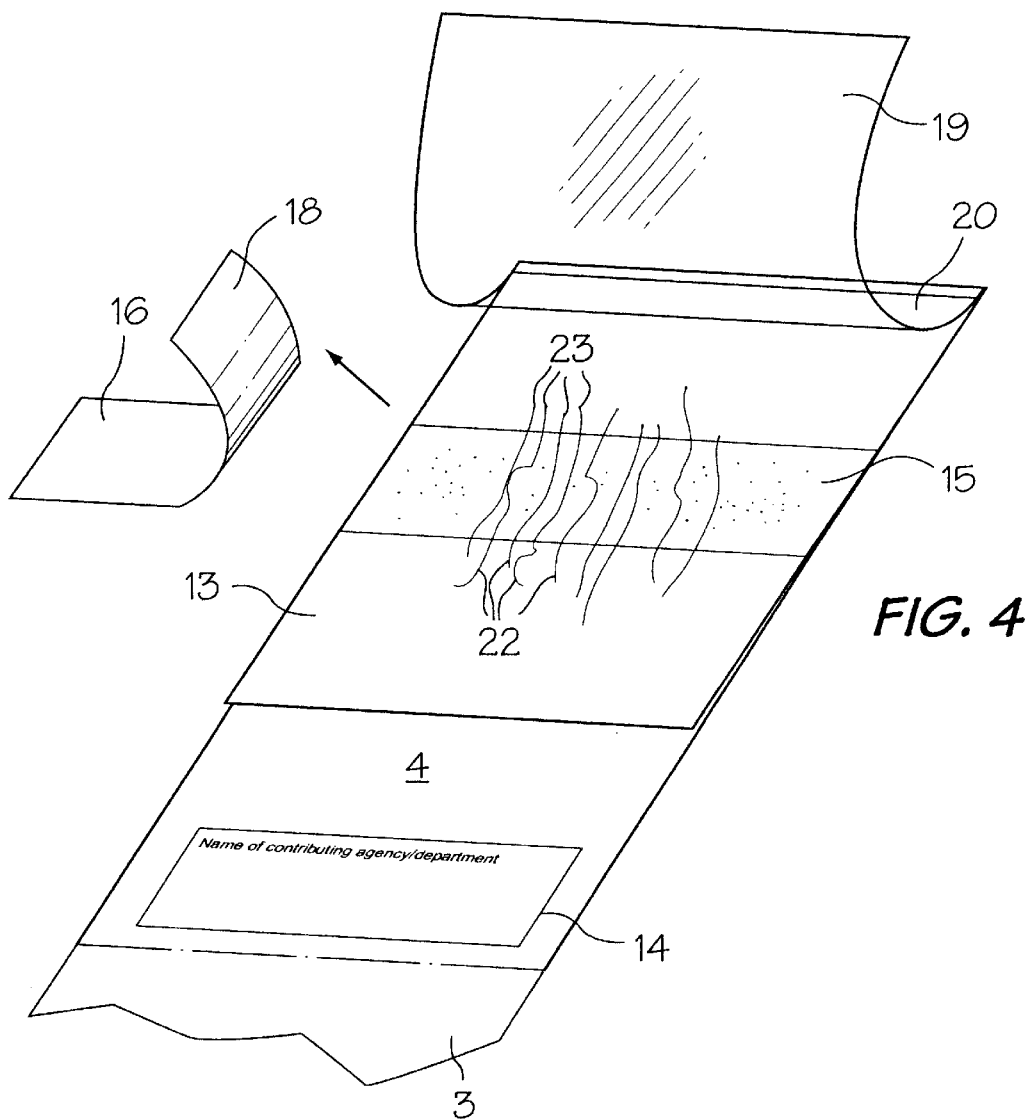
FIG. 4 is an isometric view of the card and cover of FIG. 3 with hair mounted on the card.
Figure 5:
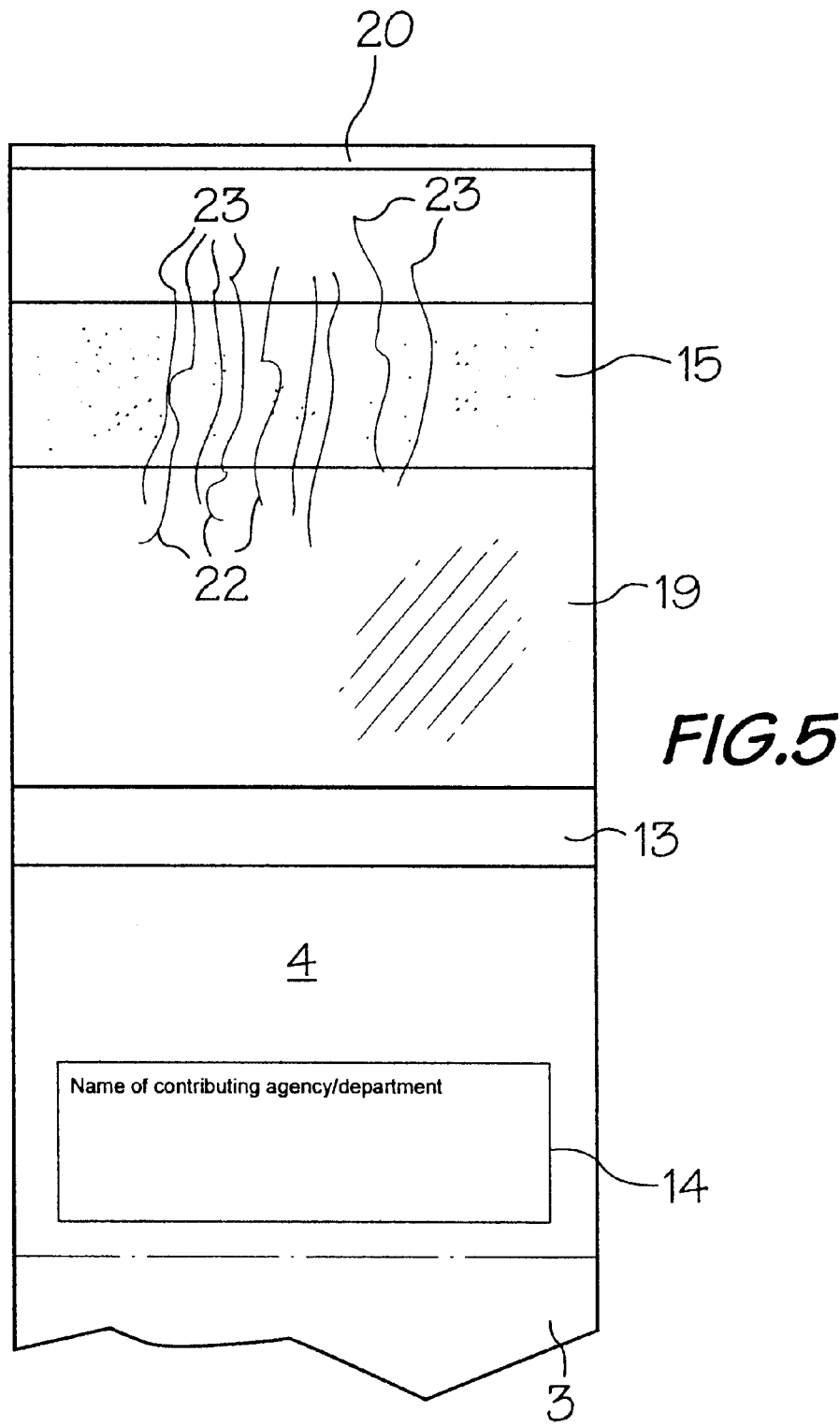
FIG. 5 is an isometric view of the card and cover of FIGS. 3 and 4 in a closed, hair carrying condition.

The other end panel 4 carries a hair root collection card 13, and a box 14 for identifying the source of the hair samples. The collection card 13 is an impermeable sheet of plastic or plastic coated material such as a synthetic plastic paper of the type available under the trademark POLYART (trademark), BXL Plastics Limited, London, England. A strip 15 of adhesive (FIGS. 3 to 5) extends across the card 13. The strip 15 is defined by a strip of two-sided tape, a suitable example of which is 3M tape #9425 with tack sheet intact. The tack sheet forms a removable cover 16 on the top or outer surface of the adhesive. The bottom surface 18 of the tack sheet is coated with wax to facilitate removal from the adhesive strip 15. The adhesive strip 15 and the cover 16 are normally covered by a clear plastic cover 19 formed of Mylar (trademark) acetate polyester film. The top end 20 of the cover 19 is glued firmly to the top end of the card 13, whereby the cover 19 can be folded open (FIGS. 3 and 4) and returned to the closed position (FIG. 5).

Before use the blank is folded along fold lines 5 and 6 to the closed position (FIG. 1) in which the outer cover 2 shields most of the card 13. In use, the outer cover 2 is unfolded to an open position (not shown). The bottom end of the card cover 19 is lifted, and the adhesive cover 16 is removed from the adhesive strip 15. Hair 22 pulled from a subject's head is placed on the adhesive strip 15 with the root sheaths 23 overlying the non-adhesive portion of the card 13 above the adhesive strip 15. The cover 19 is returned to the closed position (FIG. 5), and the kit is ready for delivery to the laboratory. In the closed position, the cover 19 sticks to the adhesive strip 15 sufficiently to stay in position during delivery to the laboratory, but can easily be opened permitting access to the hair samples. Root sheath samples are obtained by grasping the hair 22 above the adhesive strip 15 using tweezers (not shown) and then cutting the hair at a location between the tweezers and the adhesive strip.

Thus, there has been described a relatively simple, effective hair root collection kit, which is inexpensive to manufacture and easy to use. In its simplest form, the kit includes a base (the card 4) with an area of adhesive thereon for securing individual hairs to the base, whereby the root sheaths of the hair overlie a non-adhesive area on the base. Of course, it is preferable to provide a cover for the base to protect the hair samples during delivery to a laboratory.

We claim:

1. A hair root collection kit comprising a planar, non-adhesive, impermeable base; an adhesive area on said base for receiving individual hairs, a non-adhesive area on said base adjacent said adhesive area, whereby hair can be attached to the adhesive area with roots of the hair overlying the non-adhesive area of the base; a first, removable, non-adhesive cover covering said adhesive area of the base for protecting said adhesive area prior to use; a plastic sheet having one end permanently pivotally connected to said base at a location remote from said adhesive area and a second end for lifting away from the adhesive area for the attachment or removal of hair; said plastic sheet being releasably and replaceably held on the adhesive area of the base, whereby, when the said second end is lifted away from the adhesive area and the first cover removed from the adhesive area, hair can be attached to or removed from the adhesive area and, when released, the plastic sheet returns to a closed position against the adhesive area.

2. The hair root collection kit of claim 1, including a second permanent, non-adhesive, impermeable cover connected to said base and overlying said plastic sheet for protecting the plastic sheet, the first cover, any hair mounted on said adhesive area, and the roots of hairs overlying the non-adhesive area.

3. The hair root collection kit of claim 1, wherein said base is rectangular, including a top and a bottom end and a pair of side edges; and said adhesive area is a strip of adhesive extending across said base between said side edges.

4. The hair root collection kit of claim 1, wherein said base is a planar, non-adhesive, impermeable paper card; said adhesive area is a strip of adhesive extending across the card from one side edge to a second side edge thereof for receiving and retaining hair samples, and said non-adhesive areas of said card border top and bottom edges of the adhesive strip.

5. The hair root collection kit of claim 4, wherein said first, removable cover is formed of paper with a wax coating on one side thereof for removable mounting on said adhesive strip.

6. The hair root collection kit of claim 4, including a folded paper blank, said blank comprising a first panel carrying said card; and a second panel contiguous with said first panel carrying indicia for identifying the source of the hair samples.

7. The hair root collector kit of claim 6, including a third panel contiguous with said second panel for covering at least a portion of said first panel when the second panel is folded under said first panel and the third panel is folded over the first panel.

\* \* \* \* \*